(12) United States Patent
O'Sullivan et al.

(10) Patent No.: US 7,960,519 B2
(45) Date of Patent: Jun. 14, 2011

(54) EXTRACTION OF CELLULAR COMPONENTS WITH FATTY ACID DERIVATIVES

(75) Inventors: Valerie J. O'Sullivan, South Beloit, IL (US); Edward J. Conklin, Rockford, IL (US)

(73) Assignee: Pierce Biotechnology, Inc., Rockford, IL (US)

(*) Notice: Subject to any disclaimer, the term of this patent is extended or adjusted under 35 U.S.C. 154(b) by 410 days.

(21) Appl. No.: 11/915,773

(22) PCT Filed: May 30, 2006

(86) PCT No.: PCT/US2006/020667
§ 371 (c)(1),
(2), (4) Date: Dec. 6, 2007

(87) PCT Pub. No.: WO2006/130529
PCT Pub. Date: Dec. 7, 2006

(65) Prior Publication Data
US 2008/0221310 A1    Sep. 11, 2008

Related U.S. Application Data

(60) Provisional application No. 60/728,512, filed on Oct. 20, 2005, provisional application No. 60/685,780, filed on May 31, 2005.

(51) Int. Cl.
*C07K 1/14* (2006.01)
*C12N 5/04* (2006.01)
*A61K 38/00* (2006.01)

(52) U.S. Cl. ..... 530/412; 435/410; 435/341; 106/14.13; 106/14.23; 106/14.27

(58) Field of Classification Search .......... None
See application file for complete search history.

(56) References Cited

U.S. PATENT DOCUMENTS

| | | | |
|---|---|---|---|
| 5,175,190 A | 12/1992 | Burton et al. | |
| 5,434,182 A * | 7/1995 | Isaacs et al. | 514/546 |
| 5,763,586 A * | 6/1998 | Gray | 536/4.1 |
| 2003/0073209 A1* | 4/2003 | Turpen et al. | 435/183 |
| 2004/0248270 A1* | 12/2004 | Minoshima | 435/183 |

FOREIGN PATENT DOCUMENTS

| | | |
|---|---|---|
| EP | 1445261 | 8/2004 |
| WO | 90/15601 | 12/1990 |

OTHER PUBLICATIONS

"Sorbitan Fatty Acid Ester" (2010, updated) www.made-in-china.com/showroom/jimmy2011813/product-detailPqHxCQidnYWO/China-Sorbitan-Fatty-Acid-Ester-S-20-S-40-S-60-S-80-.html, pp. 1-3.*
International Preliminary Report on Patentability issued regarding International Application No. PCT/US2006/020667 (Dec. 6, 2007).
International Search Report issued regarding International Application No. PCT/US2006/020667 (Sep. 19, 2006).
Written Opinion issued regarding International Application No. PCT/US2006/020667 (Sep. 19, 2006).

* cited by examiner

*Primary Examiner* — Anand Desai
*Assistant Examiner* — Samuel Liu
(74) *Attorney, Agent, or Firm* — Thompson Hine LLP

(57) ABSTRACT

A method of treating biologic material with a composition containing at least one fatty acid derivative and/or at least one fatty alcohol, a buffer, and a salt to result in protein partitioning into an aqueous phase and an organic phase. The protein may be a membrane protein. The cells may be plant cells and/or animal cells. The proteins can be thereafter be used for downstream applications.

9 Claims, 1 Drawing Sheet

EXTRACTION OF CELLULAR COMPONENTS WITH FATTY ACID DERIVATIVES

RELATED APPLICATIONS

This application claims priority to pending U.S. Patent Application Nos. 60/685,780 filed on May 31, 2005 and 60/728,512 filed Oct. 20, 2005.

FIELD OF THE INVENTION

The present invention relates to improved methods and reagents for cell lysis and protein and nucleic acid partitioning.

DETAILED DESCRIPTION

Figure 1:
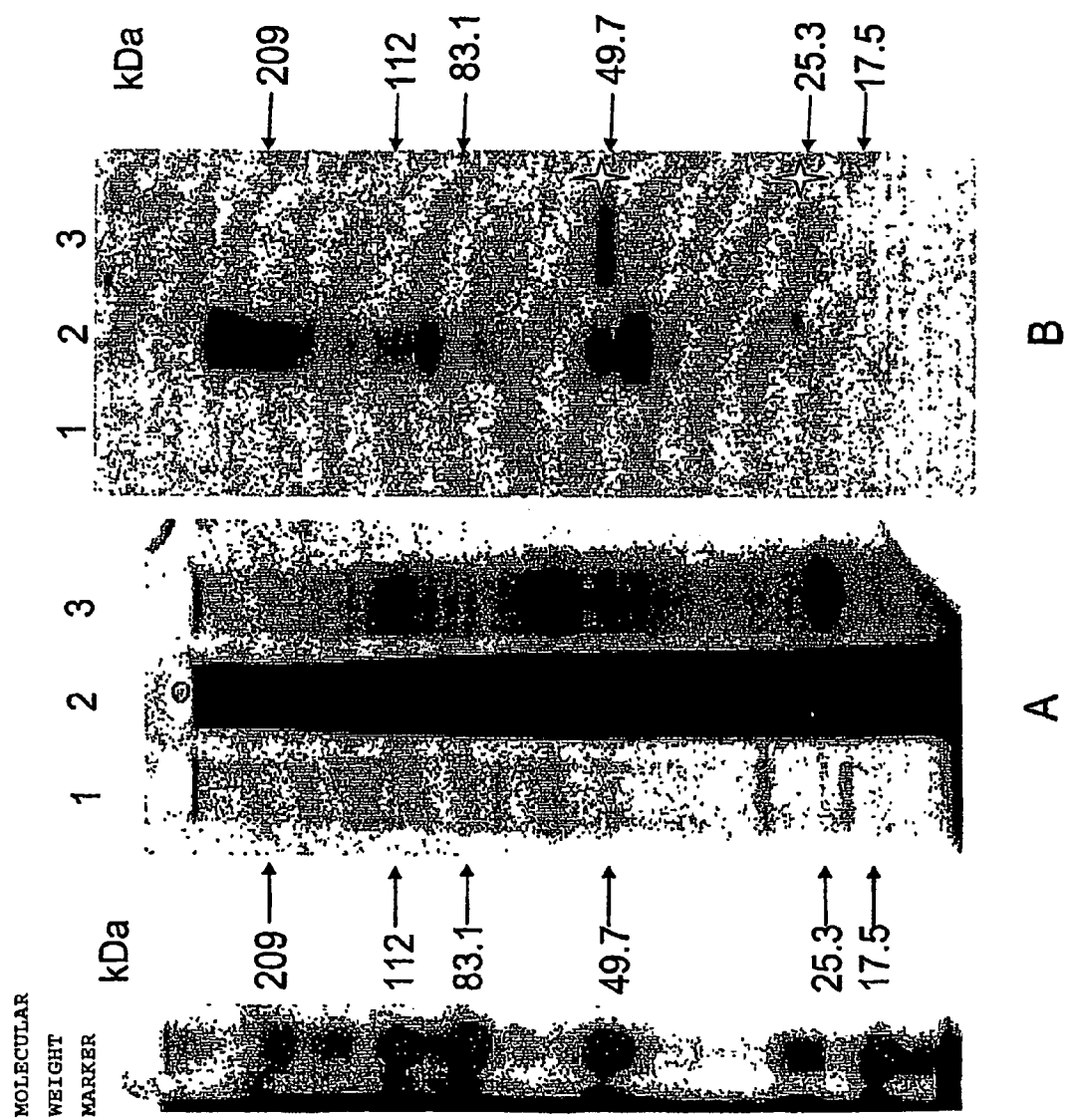
FIGS. 1A AND 1B show result of proteins separated on polyacrylamide gels detected using a stain (FIG. 1A) or antibody (FIG. 1B).

Cells from plants, mammals and fungi are lysed using an aqueous buffer containing fatty acid derivatives with mechanical abrasion. Proteins are released and partitioned into both the aqueous and organic phases. Nucleic acids are precipitated.

Without being bound by a specific theory, the fatty acid derivatives disrupt the cell walls and plasma membranes and lyse the cells, releasing the cell contents into both the aqueous buffer phase and the organic phase. As an organic solvent, the fatty acid derivatives can be added at the same time as the aqueous buffer is added at the start of cell lysis and disruption, or added before the aqueous buffer, or added after the aqueous buffer. The aqueous buffer solubilizes and stabilizes the proteins released from the disrupted cells. Mechanical abrasion during the procedure allows permeation of the reagents into the tissues or cells to achieve efficient blending which results in little or no particulate remaining that would require filtration. In one embodiment, protease inhibitors are also present to reduce or prevent protein degradation.

The tissues or cells may be fresh, frozen, dried, cultured, dehydrated, preserved, etc. Tissues or cells that may be treated by the inventive method include, but are not limited to, plant species such as *Arabidopsis*, tobacco, spinach, peas, maize and soybeans, various plant anatomical parts such as seeds, leaves, roots, stems, fruit and flowers, mammalian cultured cells and tissue, and fungi including mold cells. Samples having extremely fibrous tissue, such as plant woody stems and others known to one skilled in the art, may require enhanced mechanical agitation.

One embodiment uses fatty acid esters that contain carbon chain lengths from $C_6$ to $C_{12}$ having the chemical structure $(CH_3(CH_2)_xCOOCH_3)$ where X is 4-10. These are described herein as fatty acid methyl esters, and include other fatty acid esters having the ability to lyse plant, mammalian and fungal cells and partition the protein to the aqueous phase. In embodiments, both homogeneous and heterogeneous mixtures of these fatty acid methyl esters are used. In embodiments, mixtures of methyl esters that include predominately methyl octanoate and methyl decanoate with a small percentage of methyl hexanoate and methyl dodecanoate are used and are designated as fatty acid methyl esters. In another embodiment, primary fatty alcohols have similar extraction properties and are used. These alcohols are designated ($CH_3(CH_2)_xCH_2OH$) where X is 4-10. In another embodiment, both a fatty acid derivative and a fatty alcohol are used.

In some embodiments, the aqueous buffer contains a detergent that assists in cell lysis, protein extraction and protein solubility, a reducing agent to minimize or prevent aggregation of sulfhydryl containing proteins that are found in plants and other tissues, as well as the buffer to maintain physiological pH (between about 6.5 to about 7.5, in one embodiment pH 7.0) to maintain protein integrity. In one embodiment, HEPES base buffer (N-(2-hydroxyethyl)-piperazine-N'-2-ethanesulfonic acid) is used, but other buffers that can maintain the indicated pH can be used, such as Tris base buffer (tris (hydroxymethyl) aminomethane). In one embodiment, the detergent is TWEEN 20 (polyoxyethylenesorbitan monolaurate), and the reducing agent is Tris carboxyethyl phosphine (TECEP), but other detergents and reducing agents such as Triton® X-100 and dithiothreitol can be used, as known to one skilled in the art. In one embodiment, inhibitors of nucleic acid degradation such as RNase inhibitors are present. Such reagents are available from commercial vendors, known to persons of ordinary skills in the art, such as Pierce and Sigma-Aldrich.

In one embodiment, a working solution is prepared as mixture of the aqueous buffer (designed herein as Reagent A), the reducing agent (designated herein as Reagent B), and the fatty acid ester (designated herein as Reagent C). The components are mixed to form a colloidal suspension; in one embodiment the components are mixed just prior to cell lysis and extract to maintain optimum component activity. Other agents may be included into the work solution, for example, to optimize the analysis of the protein(s) of interest. These agents can include, but are not limited to, detergents (e.g., TWEEN 20, Triton X-100, Nonident P-40, etc.), protease inhibitors (e.g., leupeptin, aprotinin, benzamidine, etc.), antioxidants (e.g., sodium metabisulfite, sodium tetraborate, sodium diethyl dithicarbamate, etc.), and phenolic capturing reagents (e.g., insoluble polyvinylpolypyrrolidone, soluble poly(vinylpyrrolidone) [MW] 40,000)

The working solution is added to the tissue to be extracted and, in combination with mechanical agitation, the mixture is blended. Blending can be accomplished in any type of container such as commercially available polypropylene bags equipped with a mesh insert, mortar and pestle, blade operated instruments, etc. as known to one skilled in the art.

In one embodiment, Reagent A is 133 mM NaCl, 1% w/v Tween 20, and 50 mM HEPES, pH 7.0; Reagent B is 500 mM TECEP, and Reagent C is a mixture of methyl hexanoate (up to about 6%), methyl octanoate (about 50% to about 58%), methyl decanoate (about 34% to about 46%), and methyl dodecanoate (up to about 1%) based on a weight percentage of each ester.

The amount of working solution used per weight of tissue may depend upon the physical state of the tissue, for example, dehydrated, fresh, or frozen. Dehydrated tissues such as seeds required a higher ratio of working solution to weight of tissue versus fresh or frozen tissue.

In one embodiment, components of the inventive method are included in a kit. The kit may also contain reagents for downstream applications such as protein electrophoresis, to include loading buffers such as ImmunoPure® Lane Marker Sample Buffer (Pierce Biotechnologies). The kit can also contain components for sample preparation/purification such as PAGEprep® (Pierce Biotechnologies) and sample preparation/concentration such as Slide-A-Lyzer® (Pierce Biotechnologies). The kit can also contain reagents for control reactions, for example, to detect common proteins such as actin.

The Working Solution (WS) was prepared by mixing 0.99 part Reagent A with 0.01 part Reagent B and 0.75 part Reagent C (e.g., 0.99 ml of Reagent A, 0.01 ml Reagent B, and 0.75 ml of Reagent C, which was sufficient for a single extraction from 80 mg of fresh or frozen cells or tissue or 20 mg of dehydrated or dried cells or tissue). Protease inhibitor cocktail (e.g., Pierce Biotechnology Halt™ Protease Inhibitor Cocktail, Product No. 78410) was added to the WS as known to one skilled in the art and according to the manufacturer's instructions. In one embodiment, sodium metabisulfite or another antioxidant can be added to Reagent A before making the WS to inhibit oxidases and trap quinones.

The mixture was vortexed until a colloidal suspension formed. Because the two reagents rapidly separate into two phases, the WS was thoroughly mixed again immediately before addition to the tissue samples. In other embodiments, anti-oxidants, polyphenolic adsorbents and other additives can be added at this time.

The cells or tissue were placed into a container such as a polypropylene mesh bag. With three sides of the mesh bag sealed, the mesh bag was held with the open end up and the tissue was placed between the two inner screens and as low in the bag as possible. A mesh bag may hold up to 500 mg of cells or tissue (requiring about 11 ml WS). For amounts greater than about 500 mg cells or tissue, the sample can be split into amounts less than about 500 mg each for use with separate polypropylene bags or a larger mechanical grinding device (e.g., Waring Blender) can be used, with the appropriate amount of WS. The WS was added to the container (mesh bag, mechanical grinding device, etc.) containing the tissue. The open end of the mesh bag was held firmly upright while the lower portion of the mesh bag laid on a flat firm surface. A hard, round-tipped object (e.g., a fine point pen) was used to rub and massage the cells from the outside of the bag, thoroughly mixing the WS through the cells or tissue until no visibly intact tissue remained. For hard seeds such as soybeans, a pestle can be used to smash and mix the tissue into the WS. After a homogeneous mixture was achieved, the liquid was allowed to settle to the bottom of the mesh bag and was retrieved with a pipette inserted down the clear strip edge of the bag. Complete retrieval of the sample was accomplished by rubbing the bag from one end toward the side with the clear strip. The mixture was placed into a centrifuge tube and centrifuged for five minutes at 2,000-5,000×g to partition organic and aqueous phases. Filtration of the sample through filter paper or Miracloth™ was not necessary. Extracted, soluble protein was present in both phases; the lower aqueous layer and the upper organic layer. In addition to containing some of the soluble proteins, in one embodiment, the upper organic layer can be assayed for waxes, fatty acids and other long chain hydrocarbons. The two protein-containing phases can be separated by siphoning off the upper organic layer with a pipette, leaving the protein-containing aqueous layer in the tube. Alternatively, a pipette tip could be inserted through the organic layer into the aqueous layer, exerting positive pressure to gently dispense any of the organic layer caught in the pipette tip as it passed through the upper layer, carefully drawing out the protein-containing aqueous layer and transferring it to a clean tube.

In various embodiments, the protein can be extracted from tissues that are fresh, frozen, dried, or in other physical states, including tissue subjected to freeze/thaw cycles. Proteins extracted from samples that had been powdered by freeze/grinding with liquid nitrogen may no longer be active (i.e., no longer useable in functional assays).

Nucleic acids were found as a precipitant on the bottom of the tube after centrifugation. These precipitated nucleic acids can be recovered and used for downstream applications, such as isolation, purification, and quantitation of nucleic acids, reverse transcription polymerase chain reaction (RT-PCR), quantitative RT-PCT (qRT-PCR), ribonuclease protection assay (RPA), Northern blot, Southern blot, primer extension assay, mRNA quantitation assay, monitoring gene expression, genotyping, or monitoring nucleic acid-protein complexes, as known to one skilled in the art.

In one embodiment, plant tissues rich in phenolic compounds such as poplar tree leaves are subjected to a polyphenol adsorbent such as polyethylene glycol (PEG) or polyvinyl polypropylene (PVPP) that is added to the WS.

The inventive method can be performed at room temperature (e.g., about 20° C. to about 22° C.) or about 4° C. For use at 4° C., Reagents A, B, and C are pre-chilled just prior to making the working solution. The Working Solution is prepared substantially immediately before use to maintain activity of Reagent B. It separates into organic (top) and aqueous (bottom) phases, with extracted proteins partitioning into both phases. In one embodiment, the lysate is dialyzed or subjected to buffer exchange. Stabilizers that reduce protein aggregation during storage can be added to the prepared protein extract to maintain protein activity; these include 5% polyethylene glycol (PEG), 5% to 10% glycerol or mannitol, etc. as known to one skilled in the art. For long-term storage at −20° C., ethylene glycol or glycerol to a final concentration of about $10\%^{w/v}$ to about $20\%^{w/v}$ is added.

After extraction, the proteins may be used in downstream applications as known to one skilled in the art. As one example, proteins may be diluted and separated by 1-D gel electrophoresis (SDS-PAGE) using standard electrophoresis conditions. As another example, proteins may be separated by 2-D gel electrophoresis. The sample may be diluted at least 1:10 with sample loading buffer to lower the concentration of salt present in the WS (approximately 133 mM). Alternatively, the sample may be treated using PAGEprep® Advance Kit (Pierce Biotechnology Product No. 89888). As another example, protein may be assayed and the amount of protein extracted into the aqueous layer may be determined using the BCA™ Protein Assay, Reducing Agent Compatible Kit (Pierce Biotechnology Product No. 23250). As another example, the sample can be used for immunoprecipitation. As another example, protein may be isolated and purified. Following lyses and extraction, the protein is recovered and isolated by commonly utilized methods, including but not limited to those described in U.S. Patent Application Publication No. 2002/0012982.

The inventive method and reagents recover soluble protein from different cell and tissue samples in a short time, e.g., about ten minutes. The resulting protein extract is compatible with downstream applications including SDS-PAGE, 2-D gel electrophoresis, Western blotting, activity assays, protein affinity purification, etc.

Following the disclosed method for cell lysis and extraction for proteins, organelle membranes, etc, the resuspended proteins, organelle membranes, etc. are much easier to work with in further purification steps, testing for activities, etc, in comparison to an encapsulated or semi-intact form of the same material such as found in an incomplete lysis. The targets of interest, such as proteins, should result in the highest yield possible and substantially free from as many contaminating structures as possible. When a cell is lysed, such partitioning occurs. The method disrupts the cells with the least amount of disruptive force, but still retains substantially the normal structure and functional integrity of the protein(s) of interest.

In one embodiment, from the initial cell lysis and extraction of proteins, the membranes of cell organelles (e.g., mitochondria, endoplasmic reticulum, Golgi bodies, etc), are resuspended into the solution phases.

The proteins contained in these organelle membranes may be associated with and partition into either the organic phase (e.g., the methyl fatty acid layer), or the bottom aqueous phase, depending upon the length and degree of membrane spanning for the protein. A protein with multiple transmembrane domains may partition in both the lipid phase and the protein phase. This may be empirically determined and/or known by one skilled in the art. The membrane proteins embedded within the organelle are thought to be within the liquid phases of the solutions.

There was little or no protein in the pellet after the initial cell lyses and centrifugation; the majority of the protein resided in the aqueous and organic layers. However, because this is a liquid, the proteins and membrane components may not be completely soluble in these phases, so the proteins and membrane components may not exist as single entities. Rather, they may reside as a semi-soluble complex and/or colloidal suspension of patches of lipids and/or proteins in the solution phase that, with higher centrifugations, will further separate these complexes or components.

The method may be used to extract membrane proteins from plant cells and/or mammalian and non-mammalian animal cells.

Aquaporin is a channel forming protein; a protein that forms pores in cell membranes and selectively conducts water through the membrane, and prevents ions and other small molecules from passing through the membrane. These selective water channels increase membrane permeability to water and help to retain water in cells. There are several aquaporin types; each has multiple identical subunits. Examples are aquaporin -0, aquaporin-1, aquaporin-2, etc.

The intrinsic plasma membrane protein aquaporin was extracted from whole *Arabidopsis thaliana* (Columbia, wild type) plant tissue. Potentially 35 homologues belong to *A. thaliana*. The aquaporin family of proteins all share a similar structure and have six transmembrane α-helices held together by five loops. A subset of this family of proteins is the plasma membrane intrinsic protein (PIP) group. Similarities within this family can be seen when antibodies raised against one isoform can detect other isoforms within the PIP group (Santoni et al., Biochem J. 373: 289-296, 2003).

Aquaporin that had been extracted and solubilized was detected using an antibody raised against the isoforms plasma membrane intrinsic protein PIP1,1. More specifically, aquaporin was detected using rabbit anti-plasma membrane intrinsic protein 1 (PIP1), a gift of Christophe Maurel, Biochem J. 373: 289-296, 2003. All materials used were from Pierce Biotechnology, unless otherwise indicated.

Whole plant tissue was either treated as described in Boursiac et al., Plant Physiology 139 (2): 790-805, 2005, termed Method 1, or according to the present method, termed Method 2. Total protein was determined for both methods of extraction using the BCA™ Protein Assay Kit—Reducing Agent Compatible (Pierce).

In Method 1, 0.5 g plant tissue was ground using a mortar and pestle in liquid nitrogen. One ml, prechilled to −20° C., 10% trichloroacetic acid and 0.07% β-mercaptoethanol in acetone was added to the ground tissue. After thirty minutes, the mixture was centrifuged and the pellet was washed twice with −20° C. chilled 0.07% β-mercaptoethanol in acetone. The resulting pellet was resuspended in 9 M urea, 4% CHAPS, 05% Triton X-100 and 65 mM dithiothreitol. After thirty minutes of mixing, the suspension was centrifuged. The supernatant was retained as the protein containing material.

In Method 2, 0.5 g plant tissue was mechanically agitated in an aqueous buffer plus a reducing agent and a fatty acid ester mixture was used. Specifically, 5.305 ml Reagent A, 0.536 ml Reagent B, 4.02 ml Reagent C, and 50 µl of HALT protease inhibitor were used, as previously described. The suspended plant material was placed into a conical centrifuge tube and centrifuged for five minutes at 2,000×g. The upper organic layer was separated from the lower aqueous layer and each layer was placed into a clean tube. The top organic layer was treated to an equal volume of 1× gel electrophoresis sample buffer and placed on a rotating platform for twenty minutes at room temperature (about 20° C. to about 22° C.).

For both Methods 1 and 2, equal volumes of sample were loaded on a 10% polyacrylamide gel under non-reducing conditions as known to one skilled in the art. Standard Western blotting, known to one skilled in the art, was performed after protein samples were transferred to a nitrocellulose membrane. The membrane was blocked with Starting Block™ Blocking Buffer containing 0.05% TWEEN 20 for one hour, followed by incubation with the primary antibody, anti-PIP1 at a dilution of 1:5,000 in Tris buffer containing 0.05% TWEEN 20 (TBST) for another hour. After washing (3×15 minutes) with TBST, the membrane was incubated for one hour with the peroxidase-labeled mouse anti-rabbit secondary antibody. The membrane was washed as described above, followed by detection of signals by the chemiluminescent substrate, Super Signal® West Dura and exposed to X-ray film.

Results are shown in FIG. 1. FIG. 1A shows total protein detected using a silver stain. Lane (1) shows separated protein using the extract from Method 1, (1.5 µg/lane). Lanes (2) and (3) shows separated protein using the extracts from Method 2. Lane (2) (2.5 µg/lane) represents the aqueous extract and lane (3) was taken from the top, organic layer. The protein concentration from the organic layer was not determined.

FIG. 1B shows PIP1 immunodetection of aquaporin from total protein extracts. The membrane was probed with a primary antibody raised in rabbit against a 42-amino acid N-terminal peptide of PIP1. Lanes 1 through 3 are identical to those described in FIG. 1A.

Protein concentrations for each method were determined after final lyses and extraction. The protein concentrations of the total protein recovered from *A. thaliana* plant tissue were about three times higher using Method 2 than those recovered using Method 1. Table 1 summarizes the amount of protein recovered after treatment for both methods using the BCA™ Protein Assay Kit-Reducing Agent Compatible detection system. The amount of protein recovered was about 2% and 0.6% of the total weight of the plant tissue used for Method 2 and Method 1, respectively.

TABLE 1

Protein Determination of Plant Extracts for Method 1 and Method 2

|  | Method 1 | Method 2 |
| --- | --- | --- |
| Initial weight of plant tissue used | 500 mg | 500 mg |
| Total weight of protein extracted | 3.01 mg | 9.85 mg |
| Ratio of Extracted protein (mg)/Total plant weight (mg) | 0.006 | 0.02 |

The disclosed method, one embodiment of which is Method 2 above, detected and recovered membrane protein in a solution phase after cell lyses and extraction. The aquaporin protein PIP1, which is typically associated with the plasma membrane in plant tissue, was used as one embodiment of a protein for membrane protein solubilization. In FIG. 1B, lanes (2) and (3), the two stars represent the PIP1 monomer at 25 kDa and the PIP1 dimer at 50 kDa. The PIP1 protein was recovered predominately in the organic layer, although it could be detected to a lesser degree in the aqueous layer. While not being bound by a specific theory, the multiple bands in lane (2) may represent other isoforms of aquaporin or other proteins with sequence homology not yet identified. Because of the lower protein concentration recovered in Method 1, no immunoprecipitation of the PIP1 protein could be detected.

It should be understood that the embodiments and examples described are illustrative and are not limiting in any way. For example, the method may be used with other membrane proteins, for their extraction, recovery, isolation, etc. These other membrane proteins include plant and animal membrane proteins. Examples include, but are not limited to, proteins families such as the ABC (ATP binding cassette) transporters (over 100 family members and typically having two integral membrane proteins (permeases) each having six transmembrane segments, two peripheral membrane proteins that bind and hydrolyze ATP, and a periplasmic (or lipoprotein) substrate-binding protein); antiporters (about 80 family members of proteins that import or export small molecules such as glucose, amino acids, etc. against a concentration gradient); aquaporins (about 40 family members); cell wall biosynthesis proteins (about 42 family members); chloroplast and mitochodrial membrane proteins (about 100 family members, e.g., the spinach triose phosphate/phosphate translocator, mitochrondrial translocator outer member (Tom complex) proteins, translocator inner membrane (Tim complex) proteins, translocator chaperone proteins, general import pore (GIP) protein complex, etc.); lipid metabolism membrane proteins (about 167 family members); inorganic solute cotransporters (about 120 family members); ion channels (about 76 family members of protein complexes that facilitate diffusion of ions across membranes, e.g., ligand gated channel neurotransmitters, guanine nucleotide-dependent proteins (G-coupled proteins) in mammalian cell membranes, $Ca^{2+}$-ATPases such as the $Ca^{2+}$-ATPase in muscle sarcoplasmic reticulum, Na/K ATPases, other ion channels); organic solute cotransporters (about 435 family members, for example, the sodium/bile acid cotransporter family); primary pumps (about 65 members); and several dozen miscellaneous membrane proteins; cell surface proteins, dendritic cell membrane proteins, rhodopsin in the retina, photosynthetic complexes in specific membranes of purple bacteria and higher plants, etc. Therefore, various changes, modifications or alterations to these embodiments may be made or resorted to without departing from the spirit of the invention and the scope of the following claims.

The invention claimed is:

1. A method for protein recovery from a cell, the method comprising providing to at least one cell an aqueous composition comprising at least one fatty acid methyl ester derivative having the chemical structure $(CH_3(CH_2)_xCOOH_3)$ where x is 4-10 or at least one fatty acid methyl ester derivative having the chemical structure $(CH_3(CH_2)_xCOOH_3)$ where x is 4-10 and at least one $C_4$ or $C_{10}$ fatty alcohol in a concentration sufficient to disrupt the cell, at least one salt, and at least one buffer, mechanically abrading the at least one cell in the aqueous composition to result in a cell lysate, and recovering protein from the cell lysate, wherein the cell is a plant cell.

2. The method of claim 1 wherein the composition further comprises at least one of a detergent, reducing agent, ribonuclease inhibitor, antioxidant, and polyphenolic adsorbent.

3. The method of claim 1 wherein the isolated protein is capable of use in at least one of gel electrophoresis, protein quantitatlon, protein isolation, protein purification, immunoprecipitation, or activity assay.

4. The method of claim 1 wherein the at least one cell is selected from at least one of isolated cells and cells in culture.

5. The method of claim 1 wherein the cell is fresh, frozen, dried, preserved, cultured, or dehydrated.

6. The method of claim 1 wherein the cells form a tissue.

7. The method of claim 1 wherein the protein is a membrane protein.

8. The method of claim 7 wherein the protein is selected from the group consisting of aquaporin, a guanine nucleotide-dependent protein, an ion channel protein, a cell surface protein, a rhodopsin, a photosynthetic complex, and combinations thereof.

9. The method of claim 1 wherein the protein is recovered from the aqueous phase, organic phase, or both the aqueous and organic phases.

* * * * *

UNITED STATES PATENT AND TRADEMARK OFFICE
CERTIFICATE OF CORRECTION

| | | |
|---|---|---|
| PATENT NO. | : 7,960,519 B2 | Page 1 of 1 |
| APPLICATION NO. | : 11/915773 | |
| DATED | : June 14, 2011 | |
| INVENTOR(S) | : O'Sullivan et al. | |

It is certified that error appears in the above-identified patent and that said Letters Patent is hereby corrected as shown below:

Claim 1, Column 8, line 11: "ester deriva-" should read -- ester --

Claim 1, Column 8, line 12: "tive having" should read -- having --

Claim 1, Column 8, line 12: "COOH$_3$" should read -- COOCH$_3$ --

Claim 1, Column 8, line 13: "or at least" should read -- and/or at least --

Claim 1, Column 8, lines 13, 14, 15: "at least one fatty acid methyl ester derivative having the chemical structure (CH$_3$(CH$_2$(CH$_2$)$_x$COOH$_3$) where x is 4-10 and at least one C$_4$ or C$_{10}$" should read -- at least one C$_4$ or C$_{10}$ --

Claim 8, Column 8, line 39: "a photosynthetic complex," should read -- a dendritic cell membrane protein, a photosynthetic complex, --

Signed and Sealed this
Sixteenth Day of August, 2011

David J. Kappos
*Director of the United States Patent and Trademark Office*